United States Patent
Tan

(10) Patent No.: US 10,619,142 B2
(45) Date of Patent: *Apr. 14, 2020

(54) GENES WITH CODON MUTATIONS ENCODING XYLANASE

(71) Applicant: BASF ENZYMES LLC, San Diego, CA (US)

(72) Inventor: Xuqiu Tan, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/175,495

(22) Filed: Oct. 30, 2018

(65) Prior Publication Data

US 2019/0249162 A1 Aug. 15, 2019

Related U.S. Application Data

(62) Division of application No. 14/771,181, filed as application No. PCT/US2014/022484 on Mar. 10, 2014, now Pat. No. 10,131,895.

(60) Provisional application No. 61/777,348, filed on Mar. 12, 2013.

(30) Foreign Application Priority Data

May 16, 2013 (GB) .................................. 1308853.9

(51) Int. Cl.
| | |
|---|---|
| *C12N 9/24* | (2006.01) |
| *A23L 29/00* | (2016.01) |
| *C12P 19/14* | (2006.01) |
| *C11D 3/386* | (2006.01) |
| *C12P 7/06* | (2006.01) |

(52) U.S. Cl.
CPC ............ *C12N 9/2482* (2013.01); *A23L 29/06* (2016.08); *C12N 9/248* (2013.01); *C12P 19/14* (2013.01); *C12Y 302/01008* (2013.01); *C11D 3/38636* (2013.01); *C12P 7/06* (2013.01); *Y02E 50/17* (2013.01)

(58) Field of Classification Search
None
See application file for complete search history.

(56) References Cited

U.S. PATENT DOCUMENTS

| | | |
|---|---|---|
| 4,746,517 A | 5/1988 | Ducroo |
| 4,788,066 A | 11/1988 | Witt |
| 5,021,246 A | 6/1991 | Sieben et al. |
| 5,405,624 A | 4/1995 | Doncheck et al. |
| 5,536,650 A | 7/1996 | Versteegh |
| 5,762,991 A | 6/1998 | Dziondziak et al. |
| 6,365,561 B1 | 4/2002 | Vinson et al. |
| 6,380,147 B1 | 4/2002 | Speckmann et al. |
| 6,399,561 B1 | 6/2002 | Schneider et al. |
| 6,413,928 B1 | 7/2002 | Painter et al. |
| 2005/0130160 A1 | 6/2005 | Chew et al. |
| 2005/0186666 A1 | 8/2005 | Schneider et al. |
| 2005/0208178 A1 | 9/2005 | Bauer et al. |
| 2006/0003433 A1 | 1/2006 | Steer et al. |
| 2008/0058262 A1 | 3/2008 | Rasochova et al. |
| 2009/0155238 A1 | 6/2009 | Weiner et al. |
| 2011/0117067 A1 | 5/2011 | Esteghlalian et al. |

FOREIGN PATENT DOCUMENTS

| | | |
|---|---|---|
| CN | 1834250 A | 9/2006 |
| CN | 102876693 A | 1/2013 |
| WO | WO 2003/106654 | 12/2003 |
| WO | WO 2007/142954 | 12/2007 |
| WO | WO 2008/027099 | 3/2008 |
| WO | WO 2008/037757 | 4/2008 |
| WO | WO 2013/146167 | 10/2013 |

OTHER PUBLICATIONS

"Cordon usage table of Pseudomonas fluorescens"; Retrieved from the internet: URL: http://www.kazusa.or.jp/codon//cgi-bin/showcodon.cgi?species=50946; Jan. 9, 2017; XP055333382, 1 page.
Beg, Q. K. et al., (2001). "Microbial xylanases and their industrial applications: A review." Applied Microbiology and Biotechnology, 56 (3-4): 326-38.
Enkerli, J et al., (Oct. 1999). "The Enzymatic Activity of Fungal Xylanase is Not Necessary for Its Elicitor Activity." Plant Physiol. 121(2):391-397.
Le et al., (Apr. 2011). "An approach to the production of soluble protein from a fungal gene encoding an aggregation-prone xylanase in *Escherichia coli*." PLoS One 6(4):e18489.
Palackal, N et al. (Feb. 2004). "An Evolutionary Route to Xylanase Process Fitness." Protein Sci. 13(2):494-503.
O'Neill, Roger A. et al., "A fluorescence assay for enzymes that cleave glycosidic linkages to produce reducing sugars." Analytical Biochemistry, vol. 177, Issue 1, (1989)11-15.
Yin et al., (2008). "High-level expression of the xylanase from *Thermomyces lanuginosus* in *Escherichia coli*." World J Microbiol Biotechnol. 24:275-280.
International Search Report and Written Opinion for International Patent Application No. PCT/US2014/022484 dated Jul. 30, 2014.
International Preliminary Report on Patentability for International Patent Application No. PCT/US2014/022484 dated Sep. 24, 2015.
European Extended Search Report dated Jan. 19, 2017 for Application No. 14779528.0, filed Oct. 5, 2015.

*Primary Examiner* — Suzanne M Noakes
*Assistant Examiner* — Jae W Lee
(74) *Attorney, Agent, or Firm* — Richa Dhindsa

(57) ABSTRACT

The present disclosure provides for a polynucleotide sequences encoding a xylanase. More specifically, the present disclosure provides for polynucleotide sequences with codon mutations encoding a xylanase.

21 Claims, 6 Drawing Sheets
Specification includes a Sequence Listing.

Legend

Lanes 1, 5, 9 = Negative Control
Lanes 2, 6, 10 = SEQ ID NO. 3
Lane 3, 7, 11 = SEQ ID NO. 2
Lane 4, 8, 12 = SEQ ID NO. 1
Lane 13 = Molecular Weight Ladder Legend Lanes 1 = negative control
Lanes 2, 5 = SEQ ID NO: 3
Lanes 3, 6 = SEQ ID NO: 2
Lanes 4, 7 = SEQ ID NO: 1

FIG. 3

SEQ ID NO:1

ATGGCGTCGACGTTTTACTGGCACAATTGGACGGATGGTATCGGGACCGTAAATGCGACCAATG
GCTCCGACGGCAATTACAGCGTTTCATGGTCAAATTGCGGGAATTTTGTTGTTGGTAAAGGCTG
GACTACCGGATCAGCAACTAGGGTAATAAACTATAATGCCCACGCCTTTTCGCCGGTGGGTAAT
GCTTATTTGGCTCTTTATGGGTGGACGAGAAATTCACTCATAGAATATTACGTCGTTGATAGCT
GGGGGACTTATAGACCTACTGGAACTTATAAAGGCACTGTGACTAGTGATGGAGGGACTTATGA
CATATACACGACTACACGAACCAACGCACCTTCCATTGACGGCAATAATACAACTTTCACCCAG
TTCTGGAGTGTTAGGCAGTCGAAGAGACCGATTGGTACCAACAATACCATCACCTTTAGCAACC
ATGTTAACGCCTGGAAGAGTAAAGGAATGAATTTGGGGAGTAGTTGGTCTTATCAGGTATTAGC
AACAGAGGGCTATCAAAGTAGTGGGTACTCTAACGTAACGGTCTGGTGA

FIG. 4

SEQ ID NO: 2

ATGGCGTCGACGTTTTACTGGCACAATTGGACGGATGGTATTGGGACCGTAAATGCGACCAATG
GCTCCGATGGCAATTACAGCGTTTCATGGTCAAATTGCGGGAATTTTGTTGTTGGTAAAGGCTG
GACTACCGGATCAGCAACTAGGGTAATAAACTATAATGCCCACGCCTTTTCGCCGGTGGGTAAT
GCTTATTTGGCTCTTTATGGGTGGACGAGAAATTCACTCATAGAATATTACGTCGTTGATAGCT
GGGGGACTTATAGACCTACTGGAACTTATAAAGGCACTGTGACTAGTGATGGAGGGACTTATGA
CATATACACGACTACACGAACCAACGCACCTTCCATTGACGGCAATAATACAACTTTCACCCAG
TTCTGGAGTGTTAGGCAGTCGAAGAGACCGATTGGTACCAACAATACCATCACCTTTAGCAACC
ATGTTAACGCCTGGAAGAGTAAAGGAATGAATTTGGGGAGTAGTTGGTCTTATCAGGTATTAGC
AACAGAGGGCTATCAAAGTAGTGGGTACTCTAACGTAACGGTCTGGTGA

FIG. 5

SEQ ID NO: 3

ATGGCTTCGACATTCTACTGGCACAATTGGACTGATGGTATAGGGACAGTAAATGCTACCAATG
GATCTGATGGCAATTACAGCGTTTCATGGTCAAATTGCGGGAATTTTGTTGTTGGTAAAGGCTG
GACTACCGGATCAGCAACTAGGGTAATAAACTATAATGCCCACGCCTTTTCGCCGGTGGGTAAT
GCTTATTTGGCTCTTTATGGGTGGACGAGAAATTCACTCATAGAATATTACGTCGTTGATAGCT
GGGGGACTTATAGACCTACTGGAACTTATAAAGGCACTGTGACTAGTGATGGAGGGACTTATGA
CATATACGACTACACGAACCAACGCACCTTCCATTGACGGCAATAATACAACTTTCACCCAG
TTCTGGAGTGTTAGGCAGTCGAAGAGACCGATTGGTACCAACAATACCATCACCTTTAGCAACC
ATGTTAACGCCTGGAAGAGTAAAGGAATGAATTTGGGGAGTAGTTGGTCTTATCAGGTATTAGC
AACAGAGGGCTATCAAAGTAGTGGGTACTCTAACGTAACGGTCTGGTGA

FIG. 6

SEQ ID NO: 4

MASTFYWHNWTDGIGTVNATNGSDGNYSVSWSNCGNFVVGKGWTTGSATRVINYNAHAFSPVGN
AYLALYGWTRNSLIEYYVVDSWGTYRPTGTYKGTVTSDGGTYDIYTTTRTNAPSIDGNNTTFTQ
FWSVRQSKRPIGTNNTITFSNHVNAWKSKGMNLGSSWSYQVLATEGYQSSGYSNVTVW

FIG. 7

SEQ ID NO 1 vs SEQ ID NO 3

```
1:     1 ATGGCGTCGACGTTTTACTGGCACAATTGGACGGATGGTATCGGGACCGTAAATGCGACC  60
         |||||  ||||| || ||||||||||||||||| ||||||||  ||||| ||||||||| |||
3:     1 ATGGCTTCGACATTGTACTGGCACAATTGGACTGATGGTATAGGGACAGTAAATGCTACC  60

1:    61 AATGGCTCCGACGGCAATTACAGCGTTTCATGGTCAAATTGCGGGAATTTTGTTGTTGGT 120
         |||||  || || |||||||||||||||||||||||||||||||||||||||||||||||
3:    61 AATGGATCTGATGGCAATTACAGCGTTTCATGGTCAAATTGCGGGAATTTTGTTGTTGGT 120

1:   121 AAAGGCTGGACTACCGGATCAGCAACTAGGGTAATAAACTATAATGCCCACGCCTTTTCG 180
         ||||||||||||||||||||||||||||||||||||||||||||||||||||||||||||
3:   121 AAAGGCTGGACTACCGGATCAGCAACTAGGGTAATAAACTATAATGCCCACGCCTTTTCG 180

1:   181 CCGGTGGGTAATGCTTATTTGGCTCTTTATGGGTGGACGAGAAATTCACTCATAGAATAT 240
         ||||||||||||||||||||||||||||||||||||||||||||||||||||||||||||
3:   181 CCGGTGGGTAATGCTTATTTGGCTCTTTATGGGTGGACGAGAAATTCACTCATAGAATAT 240

1:   241 TACGTCGTTGATAGCTGGGGGACTTATAGACCTACTGGAACTTATAAAGGCACTGTGACT 300
         ||||||||||||||||||||||||||||||||||||||||||||||||||||||||||||
3:   241 TACGTCGTTGATAGCTGGGGGACTTATAGACCTACTGGAACTTATAAAGGCACTGTGACT 300

1:   301 AGTGATGGAGGGACTTATGACATATACACGACTACACGAACCAACGCACCTTCCATTGAC 360
         ||||||||||||||||||||||||||||||||||||||||||||||||||||||||||||
3:   301 AGTGATGGAGGGACTTATGACATATACACGACTACACGAACCAACGCACCTTCCATTGAC 360

1:   361 GGCAATAATACAACTTTCACCCAGTTCTGGAGTGTTAGGCAGTCGAAGAGACCGATTGGT 420
         ||||||||||||||||||||||||||||||||||||||||||||||||||||||||||||
3:   361 GGCAATAATACAACTTTCACCCAGTTCTGGAGTGTTAGGCAGTCGAAGAGACCGATTGGT 420

1:   421 ACCAACAATACCATCACCTTTAGCAACCATGTTAACGCCTGGAAGAGTAAAGGAATGAAT 480
         ||||||||||||||||||||||||||||||||||||||||||||||||||||||||||||
3:   421 ACCAACAATACCATCACCTTTAGCAACCATGTTAACGCCTGGAAGAGTAAAGGAATGAAT 480

1:   481 TTGGGGAGTAGTTGGTCTTATCAGGTATTAGCAACAGAGGGCTATCAAAGTAGTGGGTAC 540
         ||||||||||||||||||||||||||||||||||||||||||||||||||||||||||||
3:   481 TTGGGGAGTAGTTGGTCTTATCAGGTATTAGCAACAGAGGGCTATCAAAGTAGTGGGTAC 540

1:   541 TCTAACGTAACGGTCTGGTGA 561
         |||||||||||||||||||||
3:   541 TCTAACGTAACGGTCTGGTGA 561
```

FIG. 8

SEQ ID NO 2 vs SEQ ID NO 3

```
2:     1 ATGGCGTCGACGTTTTACTGGCACAATTGGACGGATGGTATTGGGACCGTAAATGCGACC 60
         |||||  |||| || |||||||||||||||||| |||||||| ||||| |||||||| |||
3:     1 ATGGCTTCGACATTCTACTGGCACAATTGGACTGATGGTATAGGGACAGTAAATGCTACC 60

2:    61 AATGGCTCCGATGGCAATTACAGCGTTTCATGGTCAAATTGCGGGAATTTTGTTGTTGGT 120
         ||||| || ||||||||||||||||||||||||||||||||||||||||||||||||||
3:    61 AATGGATCTGATGGCAATTACAGCGTTTCATGGTCAAATTGCGGGAATTTTGTTGTTGGT 120

2:   121 AAAGGCTGGACTACCGGATCAGCAACTAGGGTAATAAACTATAATGCCCACGCCTTTTCG 180
         ||||||||||||||||||||||||||||||||||||||||||||||||||||||||||||
3:   121 AAAGGCTGGACTACCGGATCAGCAACTAGGGTAATAAACTATAATGCCCACGCCTTTTCG 180

2:   181 CCGGTGGGTAATGCTTATTTGGCTCTTTATGGGTGGACGAGAAATTCACTCATAGAATAT 240
         ||||||||||||||||||||||||||||||||||||||||||||||||||||||||||||
3:   181 CCGGTGGGTAATGCTTATTTGGCTCTTTATGGGTGGACGAGAAATTCACTCATAGAATAT 240

2:   241 TACGTCGTTGATAGCTGGGGGACTTATAGACCTACTGGAACTTATAAAGGCACTGTGACT 300
         ||||||||||||||||||||||||||||||||||||||||||||||||||||||||||||
3:   241 TACGTCGTTGATAGCTGGGGGACTTATAGACCTACTGGAACTTATAAAGGCACTGTGACT 300

2:   301 AGTGATGGAGGGACTTATGACATATACACGACTACACGAACCAACGCACCTTCCATTGAC 360
         ||||||||||||||||||||||||||||||||||||||||||||||||||||||||||||
3:   301 AGTGATGGAGGGACTTATGACATATACACGACTACACGAACCAACGCACCTTCCATTGAC 360

2:   361 GGCAATAATACAACTTTCACCCAGTTCTGGAGTGTTAGGCAGTCGAAGAGACCGATTGGT 420
         ||||||||||||||||||||||||||||||||||||||||||||||||||||||||||||
3:   361 GGCAATAATACAACTTTCACCCAGTTCTGGAGTGTTAGGCAGTCGAAGAGACCGATTGGT 420

2:   421 ACCAACAATACCATCACCTTTAGCAACCATGTTAACGCCTGGAAGAGTAAAGGAATGAAT 480
         ||||||||||||||||||||||||||||||||||||||||||||||||||||||||||||
3:   421 ACCAACAATACCATCACCTTTAGCAACCATGTTAACGCCTGGAAGAGTAAAGGAATGAAT 480

2:   481 TTGGGGAGTAGTTGGTCTTATCAGGTATTAGCAACAGAGGGCTATCAAAGTAGTGGGTAC 540
         ||||||||||||||||||||||||||||||||||||||||||||||||||||||||||||
3:   481 TTGGGGAGTAGTTGGTCTTATCAGGTATTAGCAACAGAGGGCTATCAAAGTAGTGGGTAC 540

2:   541 TCTAACGTAACGGTCTGGTGA 561
         |||||||||||||||||||||
3:   541 TCTAACGTAACGGTCTGGTGA 561
```

SEQUENCE LISTING

<160> NUMBER OF SEQ ID NOS: 4

<210> SEQ ID NO 1
<211> LENGTH: 561
<212> TYPE: DNA
<213> ORGANISM: Artificial Sequence
<220> FEATURE:
<223> OTHER INFORMATION: Obtained from an environmental sample

<400> SEQUENCE: 1

```
atggcgtcga cgttttactg gcacaattgg acggatggta tcgggaccgt aaatgcgacc    60
aatggctccg acggcaatta cagcgtttca tggtcaaatt gcgggaattt tgttgttggt   120
aaaggctgga ctaccggatc agcaactagg gtaataaact ataatgccca cgccttttcg   180
ccggtgggta atgcttattt ggctctttat gggtggacga gaaattcact catagaatat   240
tacgtcgttg atagctgggg gacttataga cctactggaa cttataaagg cactgtgact   300
agtgatggag ggacttatga catatacacg actacacgaa ccaacgcacc ttccattgac   360
ggcaataata caactttcac ccagttctgg agtgttaggc agtcgaagag accgattggt   420
accaacaata ccatcacctt tagcaaccat gttaacgcct ggaagagtaa aggaatgaat   480
ttggggagta gttggtctta tcaggtatta gcaacagagg gctatcaaag tagtgggtac   540
tctaacgtaa cggtctggtg a                                              561
```

<210> SEQ ID NO 2
<211> LENGTH: 561
<212> TYPE: DNA
<213> ORGANISM: Artificial Sequence
<220> FEATURE:
<223> OTHER INFORMATION: Obtained from an environmental sample

<400> SEQUENCE: 2

```
atggcgtcga cgttttactg gcacaattgg acggatggta ttgggaccgt aaatgcgacc    60
aatggctccg atggcaatta cagcgtttca tggtcaaatt gcgggaattt tgttgttggt   120
aaaggctgga ctaccggatc agcaactagg gtaataaact ataatgccca cgccttttcg   180
ccggtgggta atgcttattt ggctctttat gggtggacga gaaattcact catagaatat   240
tacgtcgttg atagctgggg gacttataga cctactggaa cttataaagg cactgtgact   300
agtgatggag ggacttatga catatacacg actacacgaa ccaacgcacc ttccattgac   360
ggcaataata caactttcac ccagttctgg agtgttaggc agtcgaagag accgattggt   420
accaacaata ccatcacctt tagcaaccat gttaacgcct ggaagagtaa aggaatgaat   480
ttggggagta gttggtctta tcaggtatta gcaacagagg gctatcaaag tagtgggtac   540
tctaacgtaa cggtctggtg a                                              561
```

<210> SEQ ID NO 3
<211> LENGTH: 561
<212> TYPE: DNA
<213> ORGANISM: Artificial Sequence
<220> FEATURE:
<223> OTHER INFORMATION: Obtained from an environmental sample

<400> SEQUENCE: 3

```
atggcttcga cattctactg gcacaattgg actgatggta tagggacagt aaatgctacc    60
aatggatctg atggcaatta cagcgtttca tggtcaaatt gcgggaattt tgttgttggt   120
aaaggctgga ctaccggatc agcaactagg gtaataaact ataatgccca cgccttttcg   180
ccggtgggta atgcttattt ggctctttat gggtggacga gaaattcact catagaatat   240
```

```
tacgtcgttg atagctgggg gacttataga cctactggaa cttataaagg cactgtgact    300
agtgatggag ggacttatga catatacacg actacacgaa ccaacgcacc ttccattgac    360
ggcaataata caactttcac ccagttctgg agtgttaggc agtcgaagag accgattggt    420
accaacaata ccatcaccett tagcaaccat gttaacgcct ggaagagtaa aggaatgaat    480
ttggggagta gttggtctta tcaggtatta gcaacagagg gctatcaaag tagtgggtac    540
tctaacgtaa cggtctggtg a                                              561
```

```
<210> SEQ ID NO 4
<211> LENGTH: 186
<212> TYPE: PRT
<213> ORGANISM: Artificial Sequence
<220> FEATURE:
<223> OTHER INFORMATION: Obtained from an environmental sample

<400> SEQUENCE: 4

Met Ala Ser Thr Phe Tyr Trp His Asn Trp Thr Asp Gly Ile Gly Thr
1               5                  10                  15

Val Asn Ala Thr Asn Gly Ser Asp Gly Asn Tyr Ser Val Ser Trp Ser
            20                  25                  30

Asn Cys Gly Asn Phe Val Val Gly Lys Gly Trp Thr Thr Gly Ser Ala
        35                  40                  45

Thr Arg Val Ile Asn Tyr Asn Ala His Ala Phe Ser Pro Val Gly Asn
    50                  55                  60

Ala Tyr Leu Ala Leu Tyr Gly Trp Thr Arg Asn Ser Leu Ile Glu Tyr
65                  70                  75                  80

Tyr Val Val Asp Ser Trp Gly Thr Tyr Arg Pro Thr Gly Thr Tyr Lys
                85                  90                  95

Gly Thr Val Thr Ser Asp Gly Gly Thr Tyr Asp Ile Tyr Thr Thr Thr
            100                 105                 110

Arg Thr Asn Ala Pro Ser Ile Asp Gly Asn Asn Thr Thr Phe Thr Gln
        115                 120                 125

Phe Trp Ser Val Arg Gln Ser Lys Arg Pro Ile Gly Thr Asn Asn Thr
    130                 135                 140

Ile Thr Phe Ser Asn His Val Asn Ala Trp Lys Ser Lys Gly Met Asn
145                 150                 155                 160

Leu Gly Ser Ser Trp Ser Tyr Gln Val Leu Ala Thr Glu Gly Tyr Gln
                165                 170                 175

Ser Ser Gly Tyr Ser Asn Val Thr Val Trp
            180                 185
```

US 10,619,142 B2

GENES WITH CODON MUTATIONS ENCODING XYLANASE

CROSS REFERENCE TO RELATED APPLICATIONS

This application is a divisional of and claims the benefit and priority to U.S. patent application Ser. No. 14/771,181, filed on Aug. 27, 2015, which is a U.S. National Phase Application of PCT International Application Number PCT/US2014/022484, filed on Mar. 10, 2014, designating the United States of America and published in the English language, which is an International Application of and claims the benefit of priority to United Kingdom Patent Application No. 1308853.9, filed on May 16, 2013, and U.S. Provisional Application No. 61/777,348, filed on Mar. 12, 2013. The disclosures of the above-referenced applications are hereby expressly incorporated by reference in their entireties.

FIELD OF THE INVENTION

Polynucleotide sequences encoding a xylanase are provided. In particular, the provided sequences provide increased expression of a specific, thermostable, thermotolerant, pressure stable xylanase.

SEQUENCE LISTING

A Sequence Listing submitted as an ASCII text file via EFS-Web is hereby incorporated by reference in accordance with 37 C.F.R. § 1.821(e). The name of the ASCII text file for the Sequence Listing is SeqListVEREN2004D1.txt, the date of creation of the ASCII text file is Oct. 25, 2018, and the size of the ASCII text file is 5 KB.

FIELD OF THE INVENTION

This invention relates generally to enzymes, polynucleotides encoding the enzymes, the use of such polynucleotides and polypeptides and more specifically to enzymes having xylanase activity, e.g., endoxylanase activity, and/or catalyzing hydrolysis of internal β-1,4-xylosidic linkages or endo-β-1,4-glucan linkages; and/or degrading a linear polysaccharide beta-1,4-xylan into xylose; or, a glucanase activity, e.g., an endoglucanase activity, for example, catalyzing hydrolysis of internal endo-β-1,4- and/or 1,3-glucan linkages, a xylanase activity, and/or a mannanase activity.

Xylanases (e.g., endo-1,4-beta-xylanase, EC 3.218) hydrolyze internal β-1,4-xylosidic linkages in xylan to produce smaller molecular weight xylose and xylo-oligomers. Xylans are polysaccharides formed from 1,443-glycoside-linked D-xylopyranoses, Xylanases are of considerable commercial value, being used in the food industry, for baking and fruit and vegetable processing, breakdown of agricultural waste, in the manufacture of animal feed and in pulp and paper production. Xylanases are formed by fungi and bacteria. Arabinoxylans are major non-starch polysaccharides of cereals representing 2.5-7.1% w/w depending on variety and growth conditions. The physicochemical properties of arabinoxylans polysaccharide are such that it gives rise to viscous solutions or even gels under oxidative conditions. In addition, arabinoxylans have high water-binding capacity and may have a role in protein foam stability. AU of these characteristics present problems for several industries including brewing, baking, animal nutrition and paper manufacturing. In brewing applications, the presence of xylan results in wort filterability and haze formation issues. In baking applications (especially for cookies and crackers), these arabinoxylans create sticky doughs that are difficult to machine and reduce biscuit size. In addition, this carbohydrate is implicated in rapid rehydration of the baked product resulting in loss of crispiness and reduced shelf-life. For monogastric animal feed applications with cereal diets, arabinoxylan is a major contributing factor to viscosity of gut contents and thereby adversely affects the digestibility of the teed and animal growth rate. For ruminant animals, these polysaccharides represent substantial components of fiber intake and more complete digestion of arabinoxylans would facilitate higher feed conversion efficiencies.

Xylanases are used for a variety of industrial and commercial purposes including but not limited to: bleaching of paper pulp, increasing the brightness of pulp, degumming plant fibers, food and feed additives, baking, extraction of coffee (Beg, Q. K.; Kapoor, M.; Mahajan, L.; Hoondal, G. S. (2001). "Microbial xylanases and their industrial applications: A review." *Applied Microbiology and Biotechnology* 56 (3-4): 326-38.)

DESCRIPTION OF THE INVENTION

Enzymes are proteins that act as catalysts. Proteins are polymers of amino acids linked in dehydration reactions by peptide bonds. The identity of the amino acids and the order in which they are linked to form proteins determines a given protein's activity. This order in which amino acids are assembled into proteins (the protein "sequence") is ultimately determined by the sequence of a DNA strand which "encodes" the protein.

The three-nucleotide sequence that specifies a given amino acid to be assembled into a protein is called a "codon." The 20 amino acids built into proteins are collectively encoded by 64 tri-nucleotide codon sequences. The series of codons which specifies a protein is called an "Open Reading Frame." An amino acid may be specified by as few as one or as many as six distinct codons. A change (or mutation) in the trinucleotide sequence of a codon that does not affect the amino acid specified is called a "silent" mutation.

As a result, there are many DNA sequences capable of encoding the same protein, because the DNA sequences differ from one another only through "silent" mutations. By altering one or more of the codons which encode a given protein, it may be possible to greatly increase the amount of protein which a gene produces without affecting the sequence of the protein that is encoded.

In some embodiments, the invention comprises SEQ ID NO: 1. In some embodiments, the invention comprises the polynucleotide sequence of SEQ ID NO: 1. In some embodiments, this sequence encodes a protein. In some embodiments, this protein is an enzyme having xylanase activity.

The improved nucleotide sequence disclosed herein is given as SEQ ID NO: 1 encodes a previously disclosed xylanase enzyme that was evolved from a parent xylanase enzyme isolated from a DNA library originating from an environmental sample. The disclosed xylanase is described in PCT Publication No. WO 2003/106654, SEQ ID NO: 380 (encoded by the polynucleotide SEQ ID NO: 379 of the same publication, described herein as SEQ ID NO: 3). In some embodiments, the invention comprises the polynucleotide sequence of SEQ ID NO: 1, or fragments thereof. In some embodiments, these sequences encode a protein. In some embodiments, the protein is an enzyme having xylanase activity.

The invention comprises multiple nucleotide changes with respect to SEQ ID NO: 3. These changes are silent as to the encoded protein. The 10 base changes are set forth below. "Position" indicates the number of the nucleotide within the Open Reading Frame, with the first nucleotide of the first codon numbered as 1. The mutation is specified using the notation (old nucleotide) (position) (new nucleotide). The mutations are as follows: T6G, A12G, C15T, T33G, A42C, A48C, T57G, A66C, T69C, T72C, or any combination thereof.

In some embodiments, the mutations of the present invention, were determined by various factors including analysis of the two dimensional and three dimensional structure of the 5 prime end of the predicted mRNA structure of an ORF or gene of interest (for example SEQ ID NO. 3), as well as the preferred codons of the host, to select mutations which may enhance the expression of the protein of interest (for example, SEQ ID NO: 4). The mutations were not selected solely on the basis of the preferred codons of the host, that is, codon optimization, nor by a codon optimization program. As discussed in Example 1, two variants were created SEQ ID NO: 1 and SEQ ID NO: 2 in which silent codon mutations were introduced based on, for example, the factors mentioned above and tested for enhanced protein expression.

The base changes which distinguish SEQ ID NO: 1 from prior reported sequences encoding the disclosed cellulase, collectively and individually, result in an Open Reading Frame which leads to a higher level of protein expression than previously employed nucleotide sequences encoding the same protein.

In some embodiments, a nucleotide sequence of a xylanase derived from an environmental sample is disclosed, wherein the nucleotide sequence comprises at least one mutation selected from T6G, A12G, C15T, T33G, A42C, A48C, T57G, A66C, T69C, T72C, or any combination thereof. In some aspects of these embodiments, at least one mutation is silent as to the sequence of the encoded protein. In other aspects, at least one mutation results in the nucleotide sequence harboring at least one mutation directing expression of the xylanase at a higher level than a nucleotide sequence lacking the at least one mutation and not otherwise differing from the nucleotide sequence of the above.

In some embodiments, a nucleotide sequence encoding a xylanase is disclosed, wherein the nucleotide sequence comprises SEQ ID NO: 3 and having at least one mutation selected from T6G, A12G, C15T, T33G, A42C, A48C, T57G, A66C, T69C, T72C, or any combination thereof.

In some embodiments, a nucleotide sequence from an environmental source is disclosed having at least one mutation which increases the expression level of a protein encoded by said nucleotide sequence compared to a wild type genomic sequence. In some aspects, at least one mutation is silent.

In some embodiments, a first nucleotide sequence encoding the polypeptide of SEQ ID NO: 4 is disclosed wherein the nucleotide sequence has been mutated with respect to a second sequence encoding the polypeptide of SEQ ID NO: 4 such that the expression level of the protein is increased relative to that of the protein encoded by the second nucleotide sequence.

Expression Systems

In another embodiment, the DNA encoding the xylanase of the present invention may be introduced, either on a plasmid or stably transformed into the genome of, for example, any number of gram negative bacterial systems such as *E. coli*, *Pseudomonas* species such as *fluorescens*, *Pseudomonas putida*, *Pseudomonas aeruginosa*, *Ralstonia* species, or *Caulobacter* species. Similarly, the xylanase may be introduced into any number of gram positive bacterial expression systems such as *Bacillus* species such as *Bacillus subtilis*, *Bacillus megaterium*, *Bacillus brevis*, *Lactococcus* species such as *Lactococcus lactis*, *Lactobacillus* species, *Streptomyces* species such as *Streptomyces lividans*. Other gram negative, gram positive or unrelated eubacterial or archaeal expression systems may be used to express the xylanase.

In another embodiment, SEQ ID NO: 1 may be used to direct an increased level of expression in a number of systems in which the disclosed xylanase protein may be expressed. SEQ ID NO: 1 may be introduced into any number of expression systems to express the disclosed xylanase at an improved accumulation level. For example, SEQ ID NO: 1 may be introduced, either on a plasmid or stably transformed into the genome of, for example, any number of gram negative bacterial systems such as *E. coli*, *Pseudomonas* species such as *fluorescens*, *Pseudomonas putida*, *Pseudomonas aeruginosa*, *Ralstonia* species, or *Caulobacter* species. Similarly, SEQ ID NO: 1 may be introduced into any number of gram positive bacterial expression systems such as *Bacillus* species such as *Bacillus subtilis*, *Bacillus megaterium*, *Bacillus brevis*, *Lactococcus* species such as *Lactococcus lactis*, *Lactobacillus* species, *Streptomyces* species such as *Streptomyces lividans*. Other gram negative, gram positive or unrelated eubacterial or archaeal expression systems may be used to express SEQ ID NO: 1. In a further embodiment, SEQ ID NO: 1 may be introduced into any number of eukaryotic expression systems such as *Saccharomyces*, *Schizosaccharomyces pombe*, *Pichia pastoris*, and *Hansanuela polymorpha*.

More specifically, SEQ ID NO: 1 may be introduced into a plasmid to direct its expression. Plasmids which SEQ ID NO: 1 may be introduced include, for example, *E. coli* expression vectors of the families pQE, pET, and pASK; *Pseudomonas* expression vectors of the families pCN51 LT8, RSF1010, pWZ112T, and pMYC; *Bacillus* expression vectors of the families pBAX, pHT01, and pHIS1525; *Streptomyces* expression vectors of the families 0.16021 and pIJ2460; and *Lactococcus*: expression vectors of the families pNZ9530 and pNZ8148, for example. These examples are for demonstrative purposes and do not represent a complete set of vectors in which the polynucleotide sequence of SEQ ID NO: 1 can be expressed.

In another embodiment, the expression system can be any *Pseudomonas fluorescens* expression system known in the art, for example, the *Pseudomonas fluorescens* expression system that is commercially available from Dow Global Technologies Inc., strain DC454 (US Patent PUB. APP. NO. 20050130160 and US Patent PUB. APP. NO. 20050186666). A nucleic acid sequence encoding the xylanase enzyme or polypeptide is inserted either in the pMYC vector (Dow Global Technologies Inc., US Patent PUB. APP. NO. 20050130160) or in the pDOW1169 vector (Dow Global Technologies Inc., US Patent PUB. APP. NO. 20080058262) and then introduced into the *Pseudomonas fluorescens* host by electroporation. Those skilled in the art will know alternative vectors that can be used as embodiments of this invention.

In some embodiments, the xylanase will be expressed at least at the following expression levels: 65 U/ml, 70 U/ml, 75 U/ml, 80 U/ml, 85 U/ml, 90 U/ml, 95 U/ml, 100 U/ml, 105 U/ml, 110 U/ml, 115 U/ml, 120 U/ml, 125 U/ml, 130

U/ml, 135 U/ml, 140 U/ml, 145 U/ml, 150 U/ml, 155 U/ml, 160 U/ml, 165 U/ml, 170 U/ml, 175 U/ml, 180 U/ml, or more.

Nucleic Acids

The invention also provides isolated, synthetic, or recombinant nucleic acids comprising sequences completely complementary to the nucleic acid sequences of the invention (complementary (non-coding) and coding sequences also hereinafter collectively referred to as nucleic acid sequences of the invention).

The invention provides isolated, synthetic or recombinant nucleic acids comprising a nucleic acid encoding at least one polypeptide having a xylanase activity, wherein the nucleic acid comprises a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%. 85%, 86%, 87%, 88%, 89%, 90%, 91%, 97%, 93%, 94%, 95%, 96%, 97%, 98%, 99%, or more, or complete (100%) sequence identity (homology) to an exemplary nucleic add of the invention, including the sequence of SEQ ID NO: 1. For example, the invention provides isolated, synthetic or recombinant nucleic acids comprising a nucleic acid sequence SEQ ID NO: 1 (the exemplary polynucleotide sequences of this invention). The invention provides isolated, synthetic, or recombinant nucleic acids encoding a polypeptide comprising a sequences as set forth in SEQ ID NO: 4 (the exemplary polypeptide sequences of this invention), and enzymatically active fragments thereof.

Polypeptide

Polypeptides and peptides of the invention are isolated, synthetic, or recombinant polypeptides. Peptides and proteins can be recombinantly expressed in vitro or in vivo. The peptides and polypeptides of the invention can be made and isolated using any method known in the art. Polypeptides and peptides of the invention can also be synthesized, whole or in part, using chemical methods well known in the art. For example, xylanase polypeptides can be produced in a standard recombinant expression system (as described herein), chemically synthesized, or purified from organisms in which they are naturally expressed.

The invention provides isolated, synthetic or recombinant polypeptides having a xylanase activity, comprising an amino acid sequence having at least about 50%, 51%, 52%, 53%, 54%, 55%, 56%, 57%, 58%, 59%, 60%, 61%, 67%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 97%, 93%, 94%, 95%, 96%, 97%, 98%, 99%, or more, or has 100% (complete) sequence identity to an exemplary amino acid sequence of the invention (e.g., SEQ ID NO: 4), or an enzymatically active fragment thereof.

The invention provides isolated, synthetic or recombinant polypeptides comprising a sequence as set forth in SEQ ID NO: 4, and enzymatically active fragments thereof, and variants thereof.

In some embodiments, the invention provides polypeptides (and the nucleic acids that encode them) having a xylanase activity but lacking a signal sequence, a prepro domain, a dockerin domain, and/or a carbohydrate binding module (CBM); and in one aspect, the carbohydrate binding module (CBM) comprises, or consists of a xylan binding module, a cellulose binding module, a lignin binding module, a xylose binding module, a mannose binding module, a xyloglucan-specific module and/or a arabinofuranoside binding module.

In some embodiments, the invention provides polypeptides (and the nucleic acids that encode them) having a xylanase activity further comprising a heterologous sequence; and in one aspect, the heterologous sequence comprises, or consists of a sequence encoding: (i) a heterologous signal sequence, a heterologous carbohydrate binding module, a heterologous dockerin domain, a heterologous catalytic domain (CD), or a combination thereof; (ii) the sequence of (i), wherein the heterologous signal sequence, carbohydrate binding module or catalytic domain (CD) is derived from a heterologous enzyme; or, (iii) a tag, an epitope, a targeting peptide, a cleavable sequence, a detectable moiety or an enzyme; and in one aspect, the heterologous carbohydrate binding module (CBM) comprises, or consists of, a xylan binding module, a cellulose binding module, a lignin binding module, a xylose binding module, a mannose-binding module, a xyloglucan-specific module and/or a arabinofuranoside binding module; and in one aspect, the heterologous signal sequence targets the encoded protein to a vacuole, the endoplasmic reticulum, a chloroplast or a starch granule.

Thermostability

In one aspect, the recombinant nucleic acid of the present invention encodes a polypeptide having a xylanase activity that is thermostable. For example, a polypeptide of the invention, SEQ ID NO 4, or the variant evolved enzymes of the invention can be thermostable. The thermostable polypeptide according to the invention can retain binding and/or enzymatic activity e.g., xylanase activity, under conditions comprising a temperature range from greater than 37° C. to about 95° C., or between about 55° C. to about 85° C., or between about 70° C. to about 75° C., or between about 70° C. to about 95° C., between about 90° C. to about 95° C., between about 95° C. to about 105° C., or between about 95° C. to about 110° C. in one aspect, wherein the polypeptide can retain binding and/or enzymatic activity, e.g., xylanase activity, under conditions comprising 1° C. to about 5° C., between about 5° C. to about 15° C., between about 15° C.: to about 25° C., between about 25° C. to about 37° C. In one aspect polypeptides of the invention can retain binding and/or enzymatic activity, e.g., xylanase activity, under conditions comprising 90° C., 91° C., 92° C., 93° C., 94° C., 95° C., 96° C., 97° C., 98° C., 99° C., 100° C., 101° C., 102° C., 103° C., 103° C., 104° C., 105° C., 107° C., 108° C., 109° C., or 110° C., or more. In some embodiments, the thermostable polypeptides according to the invention retains activity, e.g., a xylanase activity at a temperature in the ranges described above, under acidic conditions comprising about pH 6.5, pH 6, pH 5.5, pH 5, pH 4.5, or pH 4 or less (more acidic), or, retain a xylanase activity under acidic conditions comprising about pH 6.5, pH 6, pH 5.5, pH 5, pH 4.5, or pH 4 or less (more acidic); or, retain xylanase activity under basic conditions comprising about pH 7, pH 7.5 pH 8.0, pH 8.5, pH 9, pH 9.5, pH 10, pH 10.5, pH 11, pH 11.5, pH 12, pH 12.5 or more (more basic) or, retain a xylanase activity under basic conditions comprising about pH 7, pH 7.5 pH 8.0, pH 8.5, pH 9, pH 9.5, pH 10, pH 10.5, pH 11, pH 11.5, pH 12, pH 12.5 or more (more basic).

Thermotolerant

In one aspect, the recombinant nucleic acid of the present invention encodes a polypeptide having a xylanase activity that is thermotolerant. For example, a polypeptide of the invention, SEQ ID NO: 4, or the variant evolved enzymes of the invention can be thermotolerant. In one aspect, the xylanase activity is thermotolerant, e.g., wherein the polypeptide retains xylanase activity alter exposure to a temperature in the range from greater than 37° C. to about 95°

C., or between about 55° C. to about 85° C., or between about 70° C. to about 75° C., or between about 70° C. to about 95° C., between about 90° C. to about 9555° C., between about 95° C. to about 105° C., or between about 95° C. to about 110° C. In one aspect, wherein the polypeptide retains a xylanase activity after exposure to conditions comprising a temperature range of between about 1° C. to about 55° C., between about 5° C. to about 1.5° C., between about 15° C. to about 25° C., between about 25° C. to about 37° C. In one aspect polypeptides of the invention can retain a xylanase activity after exposure to a temperature up to 90° C., 91° C., 92° C. 93° C. 94° C., 95° C., 96° C., 97° C., 98° C., 99° C., 100° C., 101° C., 102° C. 103° C., 104° C. 105° C., 107° C., 108° C., 109° C., or 110° C., or more. In one aspect, the xylanase activity of polypeptides encoded by nucleic acids of the invention retain activity after exposure to acidic conditions comprising about pH 6.5, pH 6, pH 5.5, pH 5, pH 4.5, or pH 4 or less (more acidic), or, retain a xylanase activity after exposure to acidic conditions comprising about pH 6.5, pH 6, pH 5.5, pH 5, pH 4.5, or pH 4 or less (more acidic); or, retain activity under basic conditions comprising about pH 7, pH 7.5, pH 8.0, pH 8.5, pH 9, pH 9.5, pH 10, pH 10.5, pH 11, pH 11.5 pH 12, pH 12.5 or more (more basic) or, retain a xylanase activity after exposure to basic conditions comprising about pH 7, pH 7.5 pH 8.0, pH 8.5, pH 9, pH 9.5, pH 10, pH 10.5, pH 11, pH 11.5, pH 12, pH 12.5 or more (more basic).

Cellulosic Digestion

Xylanases of the invention are particularly useful in baking, animal feed, beverage and wood, wood pulp, Kraft pulp, paper, paper product or paper pulp processes. In one aspect, an enzyme of the invention is thermotolerant and/or tolerant of high and/or low pH conditions. For example, in one aspect, a xylanase, a mannanase and/or a glucanase of the invention retains activity under conditions comprising a temperature of at least about 80° C., 85° C., 86° C., 87° C., 88° C., 89° C., 90° C., 91° C., 92° C., 93° C., 94° C., 95° C., 90° C., 97° C., 98° C., 99° C., 100° C., 101° C., 102° C., 103° C., 103.5° C., 104° C., 105° C., 107° C. 108° C., 109° C. or 110° C., or more, and a basic pH of at least about pH 11, or more.

The invention provides industrial, agricultural or medical applications: e.g., biomass to biofuel, e.g., ethanol, propanol, butanol and/or methanol, using enzymes of the invention having decreased enzyme costs, e.g., decreased costs in biomass to biofuel conversion processes. Thus, the invention provides efficient processes for producing bioalcohols, biofuels and/or biofuel- (e.g., bioethanol-, propanol-, butanol- and/or methanol-) comprising compositions, including synthetic, liquid or gas fuels comprising a bioalcohol, from any biomass.

In one aspect, enzymes of the invention, including the enzyme "cocktails" of the invention ("cocktails" meaning mixtures of enzymes comprising at least one enzyme of this invention), are used to hydrolyze the major components of a lignocellulosic biomass, or any composition comprising cellulose and/or hemicellulose (lignocellulosic biomass also comprises lignin), e.g., seeds, grains, tubers, plant waste (such as a hay or straw, e.g., a rice straw or a wheat straw, or any the dry stalk of any cereal plant) or byproducts of food processing or industrial processing (e.g., stalks), corn (including cobs, stover, and the like), grasses (e.g., Indian grass, such as *Sorghastrum nutans*; or, switch grass, e.g., *Panicum* species, such as *Panicum virgatum*), wood (including wood chips, processing waste, such as wood waste), paper, pulp, recycled paper (e.g., newspaper); also including a monocot or a dicot, or a monocot corn, sugarcane or parts thereof (e.g., cane tops), rice, wheat, barley, switchgrass or *Miscanthus*; or a dicot oilseed crop, soy, canola, rapeseed, flax, cotton, palm oil, sugar beet, peanut, tree, poplar or lupine; or, woods or wood processing byproducts, such as wood waste, e.g., in the wood processing, pulp and/or paper industry, in textile manufacture and in household and industrial cleaning agents, and/or in biomass waste processing.

Dietary

In one embodiment, the xylanase of the present invention may be used to pre-treat, modify, or digest a food, food additive, or dietary supplement for animals or human beings. In one embodiment, the xylanase of the present invention may be used as a food, food additive, or dietary supplement for animals or human beings. In one aspect the xylanase will treat or will act as a prophylaxis for digestive disorders. In another aspect of the present invention the xylanase will alter or enhance digestion. In another aspect of the present invention the xylanase will enhance, alter, or aid in the digestion of foodstuffs. In a further aspect of the invention the xylanase will enhance, aid, or alter in the nutrient value of foodstuffs. In a further aspect, the xylanase is active in the digestive tract, e.g., in a stomach and/or intestine.

In another embodiment, the xylanase of the invention may be used as an animal feed or an animal feed additive. In another embodiment the thermostability and/or thermotolerance of the xylanase allows for the formation of pellets without the need for a secondary agent such as salt or wax. An animal feed comprising a xylanase can be provided to an animal in any formulation known to those skilled in the art. Examples of animal feed formulations include, but are not limited to: a delivery matrix, a pellet, a tablet, a gel, a liquid, a spray, ground grain, or a powder.

The invention provides edible enzyme delivery matrix comprising a thermostable recombinant xylanase, e.g., a polypeptide of the invention. The invention provides methods for delivering a xylanase to an animal, the method comprising: preparing an edible enzyme delivery matrix in the form of pellets comprising a granulate edible carrier and a thermostable recombinant xylanase, a mannanase and/or a glucanase enzyme, wherein the pellets readily disperse the xylanase, a mannanase, and/or a glucanase enzyme contained therein into aqueous media, and administering the edible enzyme delivery matrix to the animal. The recombinant xylanase enzyme can comprise a polypeptide of the invention. The granulate edible carrier can comprise a carrier selected from the group consisting of a grain germ, a grain germ that is spent of oil, a hay, an alfalfa, a timothy, a soy hull, a sunflower seed meal and a wheat midd. The edible carrier can comprise grain germ that is spent of oil. The xylanase enzyme can be glycosylated to provide thermostability at pelletizing conditions. The delivery matrix can be formed by pelletizing a mixture comprising a grain germ and a xylanase. The pelletizing conditions can include application of steam. The pelletizing conditions can comprise application of a temperature in excess of about 80° C. for about 5 minutes and the enzyme retains a specific activity of at least 350 to about 900 units per milligram of enzyme.

Methods of Making Ethanol

The invention provides methods for making ethanol comprising contacting a starch—comprising composition with a polypeptide having a xylanase activity, wherein the polypeptide has a sequence of the invention, or the polypeptide is encoded by a nucleic acid comprising a sequence of the invention, or an enzymatically active fragment thereof. The invention provides compositions comprising a starch and a polypeptide having a xylanase activity, wherein the polypeptide has a sequence of the invention, or the polypeptide is encoded by a nucleic acid comprising a sequence of the invention, or an enzymatically active fragment thereof.

Brewing and Fermenting

The invention provides methods of brewing (e.g., fermenting) beer comprising the xylanase of the invention. In one exemplary process, starch-containing raw materials are disintegrated and processed to form a malt. An enzyme of the invention is used at any point in the fermentation process. The xylanase of the invention can be used in the brewing industry for the degradation of beta-glucans. In one aspect, the xylanase of the invention are used in the brewing industry for the clarification of the beverage. Enzymes of the invention can be used in the beverage industry in improving filterability of wort or beer, as described, e.g., in U.S. Pat. No. 4,746,517.

In one aspect, the xylanase of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15 to 25° C. for 3 to 6 days when enzyme synthesis is stimulated under the control of gibberellins. In one aspect, enzymes of the invention are added at this (or any other) stage of the process.

In one aspect, enzymes of the invention are used in mashing and conversion processes. In the brewing and fermentation industries, mashing and conversion processes are performed at temperatures that are too low to promote adequate degradation of water-soluble glucans, mannans, arabinoxylans or xylans, or other polysaccharides. These polymers form gummy substrates that can cause increased viscosity in the mashing wort, resulting in longer mash run-off, residual haze and precipitates in the final beer product due to inefficient filtration and low extraction yield.

In one aspect, enzymes of the invention are used in malthouse operations, e.g., glucanase is added to the process water, to shorten germination times and/or to encourage conversion of poor quality barley to acceptable malts. In one aspect, enzymes of the invention are used for mashing, e.g., they are added to increase wort filterability and/or improve lautering (separating the wort from the mash). In one aspect, enzymes of the invention are used in the fermentor and/or settling tank to, e.g., assist in haze clearing and/or to improve filtration. In one aspect, enzymes of the invention are used in adjunct brewing, e.g., a glucanase of the invention is added to breakdown glucans, mannans, arabinoxylans or xylans, or other polysaccharides from barley, wheat, and/or other cereals, including glycans in malt. In one aspect, enzymes of the invention are used in malt brewing, e.g., a glucanase of the invention is added to modify poor malts with high glucan content.

Glucanases, (or cellulases), mannanases, xylanases, amylases, xanthanases and/or glycosidases, e.g., cellobiohydrolases, mannanases and/or beta-glucosidases of the invention can be used in any beer or alcoholic beverage producing process, as described, e.g., in U.S. Pat. Nos. 5,762,991; 5,536,650; 5,405,624; 5,021,246; 4,788,066.

Treating Foods and Food Processing

The xylanase of the invention has numerous applications in food processing industry. For example, in one aspect, the enzymes of the invention are used to improve the extraction of oil from oil-rich plant material, e.g., oil-rich seeds, for example, soybean oil from soybeans, olive oil from olives, rapeseed oil from rapeseed and/or sunflower oil from sunflower seeds.

The xylanase of the invention can be used for separation of components of plant cell materials. For example, enzymes of the invention can be used in the separation of glucan-rich material (e.g., plant cells) into components. In one aspect, enzymes of the invention can be used to separate glucan-rich or oil-rich crops into valuable protein and oil and hull fractions. The separation process may be performed by use of methods known in the art.

The xylanase of the invention can be used in the preparation of fruit or vegetable juices, syrups, extracts and the like to increase yield. The enzymes of the invention can be used in the enzymatic treatment (e.g., hydrolysis of glucan-comprising plant materials) of various plant cell wall-derived materials or waste materials, e.g. from cereals, grains, wine or juice production, or agricultural residues such as vegetable hulls, bean hulls, sugar beet pulp, olive pulp, potato pulp, and the like. The enzymes of the invention can be used to modify the consistency and appearance of processed fruit or vegetables. The enzymes of the invention can be used to treat plant material to facilitate processing of plant material, including foods, facilitate purification or extraction of plant components. The xylanase of the invention can be used to improve feed value, decrease the water binding capacity, improve the degradability in waste water plants and/or improve the conversion of plant material to ensilage, and the like. The xylanase of the invention can also be used in the fruit and brewing industry for equipment cleaning and maintenance.

Detergent Compositions

The invention provides detergent compositions comprising one or more polypeptides of the invention and methods of making and using these compositions. The invention incorporates all methods of making and using detergent compositions, see, e.g., U.S. Pat. Nos. 6,413,928; 6,399,561; 6,365,561; 6,380,147, The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Enzymes of the invention can facilitate the removal of starchy stains by means of catalytic hydrolysis of the starch polysaccharide. Enzymes of the invention can be used in dishwashing detergents in textile laundering detergents. The actual active enzyme content depends upon the method of manufacture of a detergent composition and is not critical, assuming the detergent solution has the desired enzymatic activity. In one aspect, the amount of glucosidase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic, or zwitterionic surfactants; or, mixtures thereof.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions. In one aspect, the invention provides a method for washing an object comprising contacting the object with a polypeptide of the invention under conditions sufficient for washing. A polypeptide of the invention may be included as a detergent additive. The detergent composition of the invention may, for example, be formulated as a hand or machine laundry detergent composition comprising a polypeptide of the invention. A laundry additive suitable for pre-treatment of stained fabrics can comprise a polypeptide of the invention. A fabric softener composition can comprise a polypeptide of the invention. Alternatively, a polypeptide of the invention can be formulated as a detergent composition for use in general household hard surface cleaning operations.

DESCRIPTION OF THE FIGURES

FIG. 3 is SEQ ID NO: 1, the polynucleotide with 10 silent mutations: T6G, A12G, C15T, T33G, A42C, A48C, T57G, A66C, T69C, T72C, as compared to SEQ ID NO: 3.

FIG. 4 is SEQ ID NO: 2, the polynucleotide with 10 silent mutations: as compared to SEQ ID NO: 3.

FIG. 5 is SEQ ID NO: 3, the unmodified parent polynucleotide sequence of SEQ ID NO: 1 and 2.

FIG. 6 is SEQ ID NO: 4, the polypeptide encoded by SEQ ID NO: 1, 2, and 3.

FIG. 7 is a sequence alignment of SEQ ID NO: 1 and SEQ ID NO: 3.

FIG. 8 is a sequence alignment of SEQ ID NO: 2 and SEQ ID NO: 3.

TERMS TO DEFINE

A "codon" is a three polynucleotide sequence that specifies the identity of an amino acid to be added to a protein.

A "silent mutation" is a mutation in a codon that does not result in the specification of a different amino acid.

An "Open Reading Frame" is a series of codons that specifies the sequence of amino acids in a protein.

A base "position" is the numerical location of a base in a polynucleotide sequence, counted consecutively from the start of the open reading frame or from some other reference marker.

To "encode" a protein means to specify the amino acid sequence of that protein.

"Codon optimization" as used herein refers to modifying the codons of a gene or ORF to those that are more frequently or most frequently used in the target and host organisms, but does not alter the amino acid sequence of the original translated protein. An examples of codon optimization software is Aptagen's Gene Forge® codon optimization and custom gene synthesis platform (Aptagen, Inc., 2190 Fox Mill Rd. Suite 300, Herndon, Va. 20171). Other publicly available databases for optimized codons are available and can work equally in some embodiments as well.

A "mutation" is a change in a nucleotide sequence or an amino acid sequence compared to a reference.

A "nucleotide" refers to one of the four bases which comprise DNA sequence—Adenine (A), Thymidine (T), Guanidine (G), and Cytosine (C).

"Xylanase" is an enzyme with xylanase, mannanase, and/or a glucanase activity.

A "Unit" (abbreviated as U) is defined as 1 μmole of reducing sugars per minute at pH 6.5 and 40° C.

Example 1

Method of making enhanced expression variants.

Two variants (SEQ ID NO: 1 and NO: 2) were designed based on SEQ ID NO: 3 to mutate at the DNA level to improve the gene expression. The design of the two mutant variants takes into account the two dimensional, three dimensional structures of the DNA sequences, as well as the preferred codons of the host, all of which that may influence gene expression. The mutations were introduced on the PCR primers. Both genes were PCR-amplified and clones into the Pseudomonas vector pDOW1169 (DOW AgroSciences, IN) using standard molecular cloning techniques. The resulting expression constructs were transformed into Pseudomonas fluorescens DC454 (DOW AgroSciences, IN) and expression levels of the proteins were determined. A transformant with the SEQ ID NO:1 was designated as the lead showing significantly enhanced expression levels over the parent SEQ ID NO: 3.

Example 2

Figure 1:
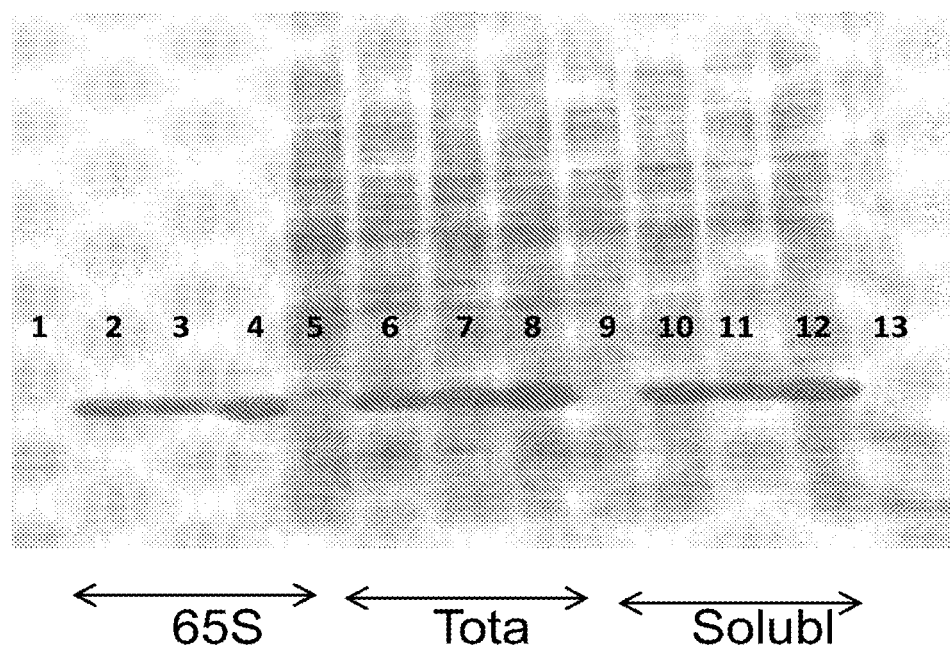
FIG. 1 is an image of SDS PAGE gel electrophoresis displaying various levels of protein expression, as described in Example 2.

Method of preparing SDS-PAGE to visually determine expression levels of variants. Criterion™ precast Tris-HCl polyacrylamide gel (Bio-rad Laboratories, Inc) was used to separate proteins. The gel was run at 150V using Tris-glycine buffer (FIG. 1). Protein loading was normalized to load proteins from 0.33 OD600 cells for each lane. See-Blue® pre-stained protein standard was used (Life Technologies). As shown in FIG. 1, the expression level of SEQ ID NO: 2 was lower than the expression level of parent SEQ ID NO: 3, and SEQ ID NO: 1.

Example 3

Method of determining relative expression levels for variants.

Figure 2:
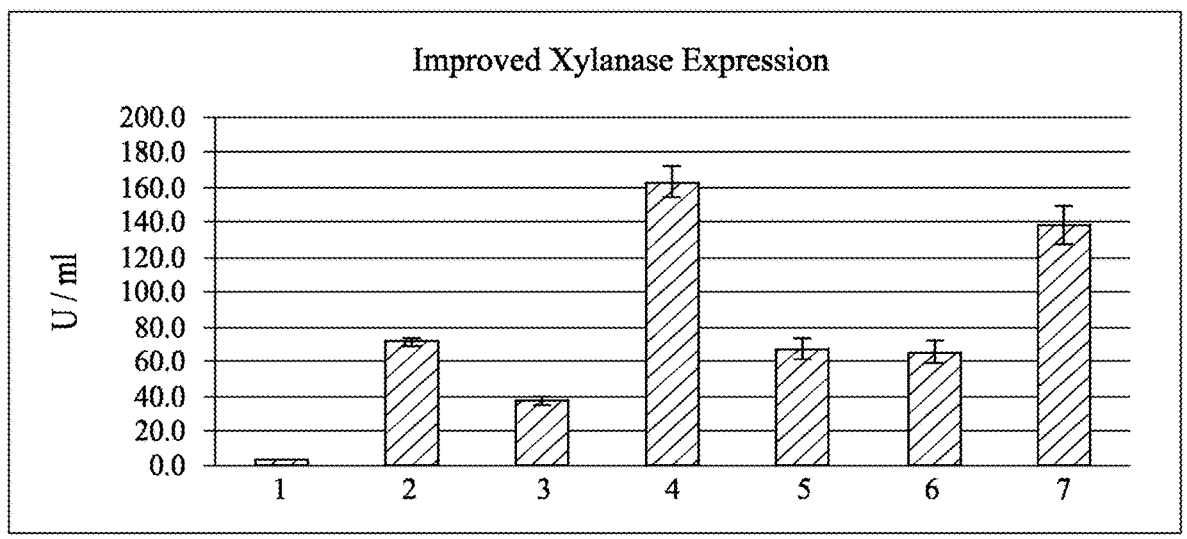
FIG. 2 is a bar graph showing the level of activity of protein preparations, as described in Example 3.

SEQ ID NO: 1, 2, and 3 genes were expressed in shake flask. The cultures were grown at 30° C. and 220 rpm to an OD600 of ~19 in a designed complex medium, and induced with 0.3 mM IPTG (Isopropylβ-D-1-thiogalactopyranoside) for 24 hours. Cells were harvested and lysed either by sonication or heat-treatment at 65° C. for 1 hour. Xylanase activity was measured by Nelson-Somogyi reducing sugar assay using wheat arabinoxylan as substrate. (Roger A. O'Neill, Alan Darvill, Peter Albersheim, A fluorescence assay for enzymes that cleave glycosidic linkages to produce reducing sugars, Analytical Biochemistry, Volume 177, Issue 1, (1989)11-15). Activity levels were measured in U/ml as shown in FIG. 2 to determine relative expression levels from each culture. A Unit (abbreviated as U) is defined as 1 μmole of reducing sugars per minute at pH 6.5 and 40° C. The specific activity for the assay in this assay was determined to be 533 units/mg protein. As shown in FIG. 2, the expression level of SEQ ID NO: 2 was lower than the expression level of parent SEQ ID NO: 3, and SEQ ID NO: 1.

What is claimed is:

1. An animal feed comprising a polypeptide encoded by a polynucleotide comprising a nucleic acid with the sequence of SEQ ID NO: 1, wherein said polypeptide has xylanase activity.

2. An animal feed comprising a polypeptide encoded by a polynucleotide comprising a nucleic acid sequence having the sequence of SEQ ID NO: 3 with the exception of at least one mutation selected from the group consisting of T6G, A12G, C15T, T33G, A42C, A48C, T57G, A66C, T69C, T72C, and any combination thereof, wherein said polypeptide has xylanase activity.

3. An animal feed comprising a polypeptide encoded by a polynucleotide comprising a nucleic acid sequence, wherein said nucleic acid sequence comprises a sequence exhibiting at least 90%, 95%, 97%, 98%, 99%, or 100% sequence identity to SEQ ID NO: 1 or SEQ ID NO: 2, and wherein said nucleic acid sequence comprises at least one mutation selected from the group consisting of T6G, A12G, C15T, T33G, A42C, A48C, T57G, A66C, T69C, T72C, and any combination thereof, relative to SEQ ID NO:1 or SEQ ID NO: 2, respectively.

4. The animal feed of claim 1, 2 or 3, wherein the polypeptide having xylanase activity is produced in a recombinant bacterial expression system.

5. The animal feed of claim 4, wherein the bacterial expression system is
    (a) a gram-negative bacteria expression system,
    (b) the gram-negative bacteria expression system of (a), wherein the gram-negative bacteria expression system is a *Pseudomonas*, *E. coli*, *Ralstonia*, or *Caulobacter* expression system, or (c) the gram-negative bacteria expression system of (b), wherein the *Pseudomonas* expression system is a *Pseudomonas fluorescens* expression system.

6. The animal feed of claim 5, wherein the xylanase that is produced is at least:
65 U/ml, 70 U/ml, 75 U/ml, 80 U/ml, 85 U/ml, 90 U/ml, 95 U/ml, 100 U/ml, 105 U/ml, 110 U/ml, 115 U/ml, 120 U/ml, 125 U/ml, 130 U/ml, 135 U/ml, 140 U/ml, 145 U/ml, 150 U/ml, 155 U/ml, 160 U/ml, 165 U/ml, 170 U/ml, 175 U/ml, or 180 U/ml.

7. The animal feed of claim 4, wherein the polypeptide:
(a) does not have a signal sequence, a proprotein sequence, or any combination thereof, or
(b) further comprises a heterologous amino acid sequence selected from the group consisting of: a signal sequence, a tag, an epitope, an N-terminal extension, a C-terminal extension, and any combination thereof.

8. The animal feed of claim 4, wherein:
(a) the polypeptide further comprises at least a second enzyme, or
(b) the polypeptide of (a), wherein the second enzyme is selected from the group consisting of: a lactase, a lipase, a protease, a catalase, a xylanase, a cellulase, a glucanase, a mannanase, an amylase, an amidase, an epoxide hydrolase, an esterase, phospholipase, transaminase, an amine oxidase, cellobiohydrolase, an ammonia lyase, and any combination thereof.

9. The animal feed of claim 2, wherein the polynucleotide has the mutation T6G.

10. The animal feed of claim 2, wherein the polynucleotide has the mutation A12G.

11. The animal feed of claim 2, wherein the polynucleotide has the mutation C15T.

12. The animal feed of claim 2, wherein the polynucleotide has the mutation T33G.

13. The animal feed of claim 2, wherein the polynucleotide has the mutation A42C.

14. The animal feed of claim 2, wherein the polynucleotide has the mutation A48C.

15. The animal feed of claim 2, wherein the polynucleotide has the mutation T57G.

16. The animal feed of claim 2, wherein the polynucleotide has the mutation A66C.

17. The animal feed of claim 2, wherein the polynucleotide has the mutation T69C.

18. The animal feed of claim 2, wherein the polynucleotide has the mutation T72C.

19. A method of making an animal feed, the method comprising:
(a) contacting a xylanase with an animal feed, wherein the xylanase is:
(i) a xylanase encoded by a polynucleotide comprising a nucleic acid with the sequence of SEQ ID NO: 1;
(ii) a xylanase encoded by a polynucleotide comprising a nucleic acid sequence having the sequence of SEQ ID NO: 3 with the exception of at least one mutation selected from the group consisting of T6G, A12G, C15T, T33G, A42C, A48C, T57G, A66C, T69C, T72C, and any combination thereof; or
(iii) a xylanase encoded by a polynucleotide comprising a nucleic acid sequence, wherein said nucleic acid sequence comprises a sequence exhibiting at least 90%, 95%, 97%, 98%, 99%, or 100% sequence identity to SEQ ID NO: 1 or SEQ ID NO: 2, and wherein said nucleic acid sequence comprises at least one mutation selected from the group consisting of T6G, A12G, C15T, T33G, A42C, A48C, T57G, A66C, T69C, T72C, and any combination thereof, relative to SEQ ID NO:1 or SEQ ID NO: 2, respectively.

20. The method of claim 19, wherein the animal feed is in the form of a pellet.

21. A method of feeding an animal, the method comprising providing the animal feed made by the method of claim 19 to an animal.

\* \* \* \* \*